US008763245B1

(12) United States Patent
Lucisano et al.

(10) Patent No.: US 8,763,245 B1
(45) Date of Patent: Jul. 1, 2014

(54) HERMETIC FEEDTHROUGH ASSEMBLY FOR CERAMIC BODY (75) Inventors: Joseph Y. Lucisano, San Diego, CA (US); Richard E. Calou, San Diego, CA (US); Mark B. Catlin, San Diego, CA (US); Joe T. Lin, San Diego, CA (US); Timothy L. Routh, San Diego, CA (US)

(73) Assignee: Glysens, Inc., a California Corporation, San Diego, CA (US)

( * ) Notice: Subject to any disclaimer, the term of this patent is extended or adjusted under 35 U.S.C. 154(b) by 2213 days.

(21) Appl. No.: 11/479,331

(22) Filed: Jun. 30, 2006

(51) Int. Cl.
*H01R 43/00* (2006.01)

(52) U.S. Cl.
USPC ............................................. 29/858; 29/842

(58) Field of Classification Search
USPC ............. 29/25.02, 25.42, 842–845, 857, 858; 333/182
See application file for complete search history.

(56) References Cited

U.S. PATENT DOCUMENTS

| | | | |
|---|---|---|---|
| 5,046,242 A | 9/1991 | Kuzma | 29/878 |
| 5,105,811 A | 4/1992 | Kuzma | 128/420.6 |
| 5,272,283 A | 12/1993 | Kuzma | 174/262 |
| 5,273,203 A | 12/1993 | Webster | 228/124.6 |
| 5,283,104 A | 2/1994 | Aoude et al. | 428/195 |
| 5,337,475 A | 8/1994 | Aoude et al. | 29/852 |
| 5,487,855 A | 1/1996 | Moeggenbord et al. | 264/63 |
| 5,782,891 A | 7/1998 | Hassler et al. | 607/37 |
| 5,821,011 A | 10/1998 | Taylor et al. | 429/181 |
| 5,855,995 A | 1/1999 | Haq et al. | 428/210 |
| 5,942,842 A * | 8/1999 | Fogle, Jr. | 333/182 |
| 6,041,496 A | 3/2000 | Haq et al. | 29/852 |
| 6,090,503 A | 7/2000 | Taylor et al. | 429/181 |
| 6,221,513 B1 | 4/2001 | Lasater | 428/629 |
| 6,812,404 B1 | 11/2004 | Martinez | 174/50.61 |
| 7,480,988 B2 * | 1/2009 | Ok et al. | 29/842 |

* cited by examiner

*Primary Examiner* — Donghai D. Nguyen
(74) *Attorney, Agent, or Firm* — DLA Piper LLP (US)

(57) ABSTRACT

A wire extends through a ceramic body. The wire comprises a material selected from the group consisting of platinum, palladium, rhodium, iridium, osmium and alloys of platinum, palladium, rhodium, iridium, and osmium. The wire directly contacts the ceramic body to form a substantially hermetic seal between the ceramic body and the wire.

15 Claims, 5 Drawing Sheets

HERMETIC FEEDTHROUGH ASSEMBLY FOR CERAMIC BODY

BACKGROUND

The use of feedthroughs, or conductive vias, is common in electronic fabrication and packaging where electrical continuity or electrical connection is required between two sides of a non-conductive body, where such body also forms part of a housing or package for electronic circuitry. Such bodies, when produced in a substantially planar configuration and configured for attachment of electronic circuitry, are commonly referred to as "substrates," but may be utilized in other geometric configurations, such as cylinders, cubes, spheres, or sections thereof, with or without attached circuitry. Feedthroughs are particularly suited for use in electrochemical sensing devices where electrodes on one side of a substrate need to communicate electrically with circuitry that is physically in communication with the other side of the substrate. Such circuitry often includes integrated circuits. In many electrochemical sensing devices, such as those designed for implantation in humans, the feedthrough must also be a moisture-resistant barrier in order to protect the electronic circuitry from moisture damage due to the fact that the electrodes come into contact with body fluids. Acceptably impervious barrier structures are commonly referred to as "hermetic," and the term is often associated with a transmission rate for helium of $10^{-8}$ cc-atm/sec or less, as in, for example, MIL-STD 883D. Feedthroughs also find application in vacuum systems, in the construction of batteries, and in various types of instrumentation.

Ceramic is widely used as a material for mounting and/or housing electronic circuitry. It is also a dielectric and can therefore serve as a mounting surface for various electrical contacts and electronic components which can be electrically connected using conductive traces, solder, conductive pastes, wire bonding, etc. Many types of ceramics are also biocompatible materials, making them suitable for implantation in the human body. In the past, various methods have been developed for providing feedthroughs in ceramic bodies by the addition of discrete, multi-component assemblies that include metal, glass, and ceramic elements. Such feedthrough assemblies are complex, costly, and unsuitable for fabrication into high-density multi-conductor configurations.

Ceramic materials can be readily formed and machined when in the so-called "green" state. The green state is a form of the material comprising a mixture of the ceramic in particulate form and a volatile organic binder that supports the particles. The presence of this organic binder is also an indicator of whether the ceramic material has been fired. An example of such material, and methods for forming it into desired shapes, is described in U.S. Pat. No. 5,487,855 of Moeggenborg, et al. assigned to Nalco Chemical Company.

Many ceramic materials are supplied commercially in the green state. During the firing process, the polymer binder material is driven off and/or decomposed at elevated temperature, allowing the ceramic particles to closer approximate each other and become sintered or fused. The loss of volatile binder material and the sintering of the ceramic particles in the firing process lead to a shrinkage of the part during the firing process. Ceramic materials typically have very high strength after firing, but a much lower strength prior to firing, when in the green state. Depending on the formulation, green ceramic materials may possess varying degrees of ductility.

U.S. Pat. Nos. 5,855,995 and 6,041,496 of Haq et al. assigned to Medtronic, Inc., disclose a ceramic substrate for an implantable medical device such as a heart pacemaker. The substrate includes a stack of ceramic layers. External metallization layers are connected by internal metallization layers and paste-filled vias that are fired to achieve hermeticity. The paste contains 20% or less by weight high temperature ceramic powder and about 80% or more by weight powdered ruthenium, platinum, or other metals. Upon firing at a temperature between 1400° C. and 1800° C., the ceramic powder in the via-fill paste causes the via-fill material to adhere to the walls of the via.

U.S. Pat. No. 5,273,203 of Webster assigned to General Electric Company discloses a hermetic seal for a conductive feedthrough through a ceramic component. The feedthrough comprises a small lead made of a platinum or palladium core with a thin copper plating which is surrounded by a copper collar. A copper-copper oxide eutectic seals the gap between the lead and the walls of the aperture in the ceramic through which the lead extends. The requirement of a potentially corrodible copper component is unacceptable for applications in which the external side of the feedthrough functions as an electrode in an aqueous environment.

U.S. Pat. Nos. 5,821,011 and 6,090,503 of Taylor et al. assigned to Medtronic, Inc. disclose a body implanted device with an electrical feedthrough in the wall of a titanium or titanium alloy container. The patent claims a center pin or terminal that is surrounded by a special glass material which is highly resistant to the corrosive effects of organic electrolytes found in batteries or the corrosive effects of direct contact with body fluids. This construction requires the incorporation of a glass material to promote the seal around the center pin.

U.S. Pat. No. 6,221,513 of Lasater assigned to Pacific Coast Technologies, Inc. discloses methods for hermetically sealing an interface of ceramic materials to an interface surface of titanium-containing alloys using a titanium-nickel alloy filler material. The filler material is additionally in contact with a ceramic component containing zirconia, whereby the titanium-nickel material forms a liquid at less than 1100° C. in the presence of the metallic and ceramic components.

U.S. Pat. No. 5,782,891 of Hassler et al. also assigned to Medtronic, Inc. discloses a packaging arrangement for an implantable medical device including a ceramic enclosure and a multi-layered substrate having multiple feedthroughs. The multi-layered substrate couples to the ceramic enclosure at the edges around an opening.

U.S. Pat. Nos. 5,283,104 and 5,337,475 of Aoude et al. assigned to International Business Machines Corporation disclose compositions for producing conductive vias in multi-layer ceramic substrates having circuits, without cracking and/or loss of hermetic sealing. A via paste mixture is introduced in the via. The mixture contains glass spheres smaller than 10% of the via size and metallic spheres less than ⅓ the size of the glass spheres. The metallic spheres are made of copper, copper-beryllium, copper-iron-cobalt alloys, or other materials. Such metals are not appropriate for use with electrochemical sensors in contact with electrolytic fluids, and the vias formed by this process could not serve directly as electrodes. Appropriate electrode materials such as platinum are not included.

U.S. Pat. No. 6,812,404 of Martinez assigned to Medtronic, Inc. discloses feedthrough assemblies and methods for creating feedthrough assemblies with brazed seals and a conductive material that provides electrochemical corrosion protection of the brazed seals. The assemblies require the braze material to provide the hermetic sealing between the terminals and the surrounding insulators and further require another electrically conductive material to protect the braze material from the corrosive effects of contact with aqueous fluids.

U.S. Pat. Nos. 5,046,242, 5,105,811, and 5,272,283 of Kuzma assigned to the Commonwealth of Australia disclose methods for creating feedthrough assemblies and a cochlear prosthetic package that utilizes these feedthroughs. The feedthrough assemblies rely on hollow tubes that are placed in the ceramic bodies and are welded closed on at least one end to provide a hermetic assembly.

SUMMARY OF THE INVENTION

In accordance with an embodiment of the invention, a feedthrough assembly includes a ceramic body. A wire extends through the ceramic body. The wire comprises a material selected from the group consisting of platinum, palladium, rhodium, iridium, osmium, and alloys of platinum, palladium, rhodium, iridium, and osmium. The wire directly contacts the ceramic body to form a substantially hermetic seal between the ceramic body and the wire.

In accordance with another embodiment of the invention, a feedthrough assembly includes a ceramic body. A plurality of wires extends through the ceramic body. The wires each comprise a material selected from the group consisting of platinum, palladium, rhodium, iridium, osmium; and alloys of platinum, palladium, rhodium, iridium, and osmium. The wires directly contact the ceramic body to form a substantially hermetic seal between the ceramic body and each wire.

In accordance with another embodiment of the invention, a method of forming a feedthrough assembly in a ceramic body is included. The first step is providing a green ceramic body. The next step of the method is forming a hole in the green ceramic body by any means, including but not limited to, utilizing the wire itself to form the hole, said hole having a first diameter. The next step of the method involves inserting a wire through the hole or leaving the wire to reside in place, if it was used to form the hole. The wire comprises a material selected from the group consisting of platinum, palladium, rhodium, iridium, osmium, and alloys of platinum, palladium, rhodium, iridium, and osmium, said wire having a second diameter. The last step of the method is to fire the green body with the wire in place.

In accordance with another embodiment of the invention, a method of forming a feedthrough assembly in a ceramic body is included. In the method, green ceramic material, in a mold, is formed around a wire, and the green feedthrough assembly is then removed from the mold. The wire comprises a material selected from the group consisting of platinum, palladium, rhodium, iridium, osmium, and alloys of platinum, palladium, rhodium, iridium, and osmium, said wire having a second diameter. The last step of the method is to fire the green body with the wire in place.

In accordance with yet another embodiment of the invention, an implantable glucose-level sensing device includes a container having a ceramic body forming at least a portion thereof. At least two electrodes are formed on an exterior surface of the ceramic body. A plurality of feedthrough assemblies are formed in the ceramic body, each connected to a corresponding one of the electrodes. The feedthrough assemblies comprise a material selected from the group consisting of platinum, palladium, rhodium, iridium, osmium, and alloys of platinum, palladium, rhodium, iridium, and osmium. The feedthrough assemblies directly contact, or alternatively comprise, a portion of the ceramic body in such a way as to form substantially hermetic seals between the ceramic body and the feedthrough assemblies. A membrane layer establishes ionic contact between the electrodes. A glucose oxidase element is supported adjacent one of the electrodes. A circuit mounted inside the container is electrically connected to the electrodes via the feedthrough assemblies and determines a glucose level in a body fluid contacting the exterior of the device.

DETAILED DESCRIPTION

The entire disclosure of co-pending U.S. patent application Ser. No. 10/925,074 of Mark B. Catlin and Dr. Joseph Y. Lucisano filed Aug. 23, 2004 is hereby incorporated by reference.

There is a need for a feedthrough in a ceramic body that: (1) provides a reliable hermetic seal to prevent moisture, gases, or other vapors on one side of the ceramic body from penetrating the feedthrough and interfering with, reacting with, or damaging electronic circuitry or other sensitive structures or materials on the other side of the ceramic body; (2) allows a multitude of separate electrical pathways to be constructed in a relatively small area; (3) can be constructed using chemically, electrolytically, and physically stable materials, for example materials that are acceptable for implantable applications (otherwise referred to as "biocompatible materials"); and (4) is fabricated using a simplified technique.

Figure 1:
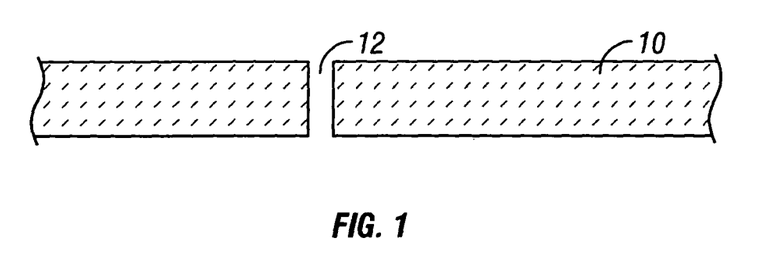
FIGS. 1-3 are a sequence of diagrammatic vertical sectional views illustrating a method of fabricating a feedthrough assembly in accordance with an embodiment of the invention.

Referring to FIG. 1, in accordance with an embodiment of the invention, a method of forming a feedthrough assembly in a ceramic body includes the steps of providing a green ceramic body 10 (FIG. 1) and forming a hole 12 in the green ceramic body 10. The green ceramic body may be made of a powdered inorganic component comprising oxides, carbides, borides, nitrides and silicides of aluminum, zirconium, beryllium, silicon, titanium, yttrium, hafnium, magnesium, and zinc, combined with an organic binder and optionally other organic compounds. The body may be produced using conventional green ceramic forming techniques, such as roll compaction, tape casting, pressing, or molding.

Volume ratios of inorganic powder to organic binder may range from 50:50 to 100:0 with a range of 70:30 to 95:5 being preferred, and a range of 80:20 to 90:10 being most preferred. Major constituents of preferred inorganic powders are: (1) alumina, for example A-16, manufactured by Alcoa and C90LSB, manufactured by Alcan Chemicals; (2) yttria-stabilized zirconia, for example HSY-3 manufactured by Daiichi Kigenso Kagaku Kogyo Co., Ltd.; and (3) mixtures and combinations thereof, although numerous other ceramic powders and mixtures can be used. A wide range of particle sizes is acceptable, so long as the particles sinter during firing such that the bulk of the green ceramic body 10 becomes hermetic after firing. Consistent with conventional ceramic processing guidelines, powders with median particle sizes ranging from 0.2 microns to 2 microns are preferred. Numerous organic binders and binder systems are suitable, so long as they can be decomposed or otherwise removed at a temperature below the sintering temperature of the ceramic powder. Examples of acceptable binders include various waxes, polyvinyl acetate, polyvinyl alcohol, polymethylmethacrylate (PMMA), polyvinyl butyral, polyethylene glycol (PEG), polyethylene oxide, ethylene-vinyl acetate copolymers, and numerous other compounds, as single components or mixtures, either plasticized by incorporation of additional organic compounds, or unplasticized. The binder may also include one or more dispersing agents, wetting agents, or fillers.

Because of the innate chemical stability of fired ceramics that contain high concentrations of alumina, inorganic powder formulations containing 95% or greater alumina are preferred, and formulations containing 99% or greater are most preferred, including, for example, formulations that provide ceramics meeting the composition requirements of industry standard ASTM F 603-00. In preferred formulations, the 1% to 5% other oxides in the inorganic powder typically include oxides of lower melting point, which function as high temperature flux to aid in sintering. Other formulations may be employed when chemical stability requirements are less stringent, including other combinations of ceramic powders with varying amounts of glasses. Formulations containing zirconia, and/or yttria-stabilized zirconia, alone or in combination with alumina, may be selected when mechanical strength is of high importance.

The hole 12 may be formed by mechanical drilling or punching, or it may be formed with a high pressure water stream, or it may be formed with a laser, or it may be formed by molding, or it may be formed in any other suitable way that allows control over both its location and diameter. The thickness of the green ceramic body 10 in the region of the hole 12 may be of any dimension appropriate to meet the mechanical strength requirements for the intended application of the assembly, with a minimum thickness of 0.002 inch being preferred and a minimum thickness of 0.025 inch being most preferred.

The next step of the method involves inserting a wire 14 (FIG. 2) through the hole 12. A small drop of liquid, for example water or an organic liquid such as cyclohexanone, may optionally be applied to the hole 12 as a lubricant to aid insertion of the wire. When using such a lubricant, it is important not to select a compound that acts too aggressively as a solvent for the organic binder system in the green ceramic, because the disruption of the green ceramic produced by application of the lubricant could result in the fired assembly being non-hermetic. The term "wire" is used herein to denote a metallic, electrically-conductive structure that: (1) may be of various uniform and non-uniform cross-sectional geometries, the most typical being uniform circular; and (2) has at least one solid cross section contained within the ceramic body. The wire 14 comprises a material selected from the group consisting of platinum, palladium, rhodium, iridium, osmium, and alloys of platinum, palladium, rhodium, iridium, and osmium, and may have one or both ends tapered or rounded to facilitate insertion. Platinum and the other metals listed for the wire 14 are specified not only for their electrical conductivity, but also because they are biocompatible, resist corrosion in the presence of liquids, and have melting points greater than the required firing temperature of the ceramic. Wires made from platinum and iridium are preferred, and wires made from pure platinum, of a minimum 99% purity, are most preferred. Wire diameters may range from 0.001 inch to 0.100 inch, with 0.002 inch to 0.040 inch being preferred, and 0.005 inch to 0.020 inch being most preferred.

Figure 2:
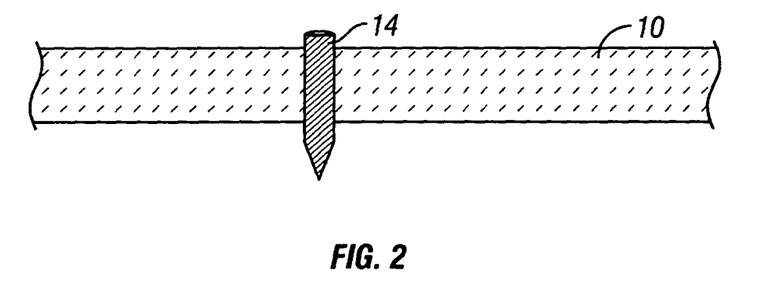

In another embodiment, the wire 14 is inserted through the green ceramic body 10 by pushing or pressing the wire 14 through a solid green ceramic body, without first forming a hole, eliminating the need to separately produce the hole 12.

In another embodiment, the green ceramic body 10 is formed around the wire 14 by molding or pressing green ceramic material in a mold that contains the wire 14, eliminating the need to separately produce the hole 12. Such a process is commonly referred to as "insert molding."

In another embodiment, the green ceramic body 10 is formed around the wire 14 by first forming a hole 12 in the green ceramic body, placing a wire 14 in the hole 12, and then pressing the assembly in a mold to cause the green body material to flow into close contact with the wire 12.

In the embodiments, the green ceramic body 10 containing the wire 14 is fired to vaporize the organic compounds in the green material and to sinter the ceramic particles, resulting in a rigid, solid structure of high density. Firing is preferably accomplished by heating the green ceramic body in air to temperatures between about 1500 and about 1700 degrees Celsius for periods of at least about 10 minutes to 4 hours.

In one embodiment, the feedthrough assembly 16 (FIG. 3) has a disc-shaped electrode 18 connected to one end of the wire 14 on an exterior side of the fired ceramic body 10' and a disc-shaped contact 20 connected to the other end of the wire 14 on an interior side of the fired ceramic body 10'. The electrode 18 and contact 20 can be separate pieces of metal formed and bonded to the wire 14 and made of the same metal as the wire 14. Preferably the electrode 18 and contact 20 are formed by trimming the wire above the surface of the fired ceramic body 10' and flattening the opposite ends of the wire 14 into a disc-shaped configuration. Preferred methods for flattening the ends of wire 14 include grinding and polishing using diamond-based abrasive media, which can also serve to flatten the exposed ceramic surfaces, which may be slightly warped or rough immediately after firing.

Figure 3:
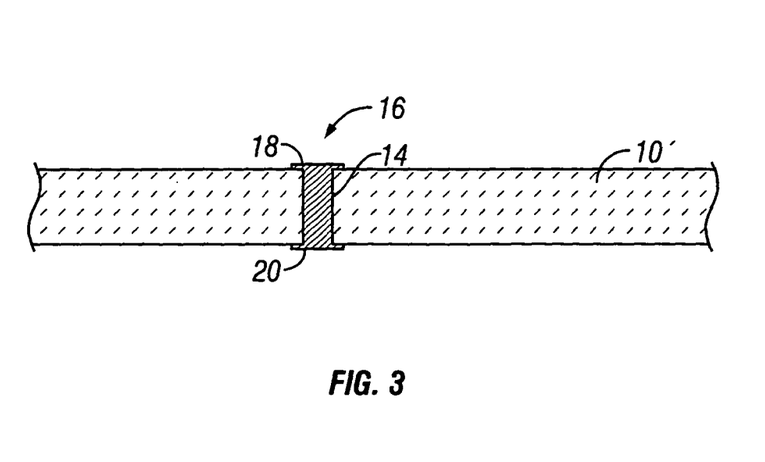

The diameter of the hole 12 in the green body 10 and the diameter of the wire 14 are selected such that a close fit is achieved upon insertion of the wire 14 into the hole 12 in the green ceramic body 10 and, after shrinkage of the green ceramic body 10 during firing, a substantially hermetic seal is formed between the sintered ceramic and the wire 14. It is very important that the feedthrough assembly 16 provide a substantially hermetic seal, i.e. that moisture will not creep or diffuse from one side of the fired ceramic body 10' to the other side between the fired ceramic body 10' and the wire. It is believed that what is termed in the art a "diffusion bond" or "reaction bond" may be formed between the wire 14 and the fired ceramic body 10' which provides a high degree of hermeticity. Tests have proven that there is a wide range of allowable diameters of the wire 14, diameters of the hole 12, and thicknesses of the green ceramic body 10 that can be used to achieve the desired hermeticity. The diameter of the hole 12 should be close in dimension to the diameter of the wire 14, but it should not be so small that cracking or significant disruption of the green ceramic material occurs upon insertion of the wire or firing thereafter. In practice, a 0.0005 inch to 0.002 inch differential in diameters, with the wire diameter either larger or smaller than the hole diameter, is preferred to produce acceptable results, although larger differentials may be acceptable when using large diameter wires (for example, greater than 0.020 inch diameter).

In the practice of the method, the initial choice of green body 10, first diameter, second diameter, and wire is herein referred to as an initial configuration. The method of the invention provides means for iterative refinement of the initial configuration to achieve successful levels of hermeticity in the completed feedthroughs.

In an initial configuration, the first diameter may be greater than, equal to, or less than the second diameter. The success rate of hermeticity after firing is dependent upon the choice of first and second diameters and upon the material properties of the green body 10. Brittle green ceramic bodies may fracture upon wire insertion or during early or intermediate stages of the firing process if the first diameter is significantly smaller than the second diameter, thus decreasing success rates. More ductile green bodies may be capable of plastic deformations which can lead to higher success rates with first diameters that are equal to or smaller than the second diameters.

In the method, the green ceramic body 10 with inserted wire 14 is fired to sinter the green ceramic body 10 and produce the fired ceramic body 10'. The diameter of the hole in the green body and the diameter of the wire are selected such that the shrinkage of the ceramic body during firing results in the development of a substantially hermetic seal between the sintered ceramic body and the wire. Techniques are disclosed to guide selection and optimization of the hole size and wire size to achieve substantially hermetic seals.

The wire 14 is preferably in intimate association with the fired ceramic body 10' throughout the length of its contact, although the invention requires only that the wire 14 and the fired ceramic body 10' be circumferentially hermetically joined in at least one location along the length of the wire 14.

Figure 4:
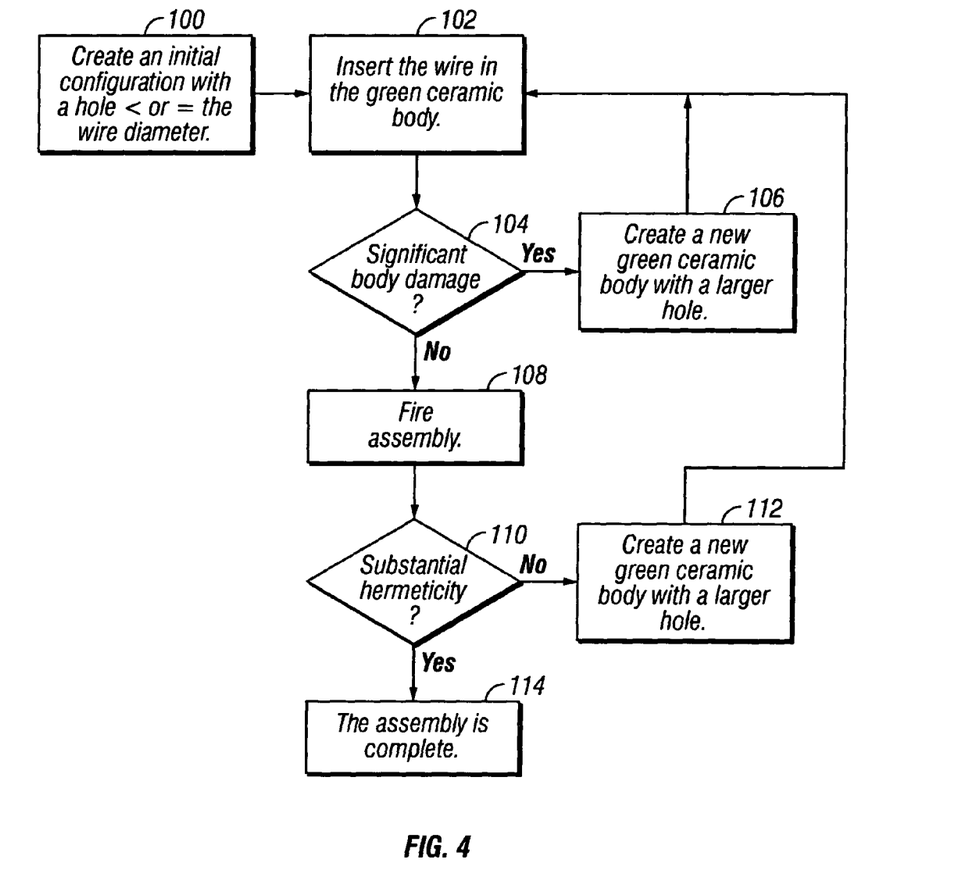
FIG. 4 is a flow diagram of an exemplary method of producing a substantially hermetic feedthrough in a ceramic body where an initial configuration includes the first diameter less than, or equal to, the second diameter.
Figure 5:
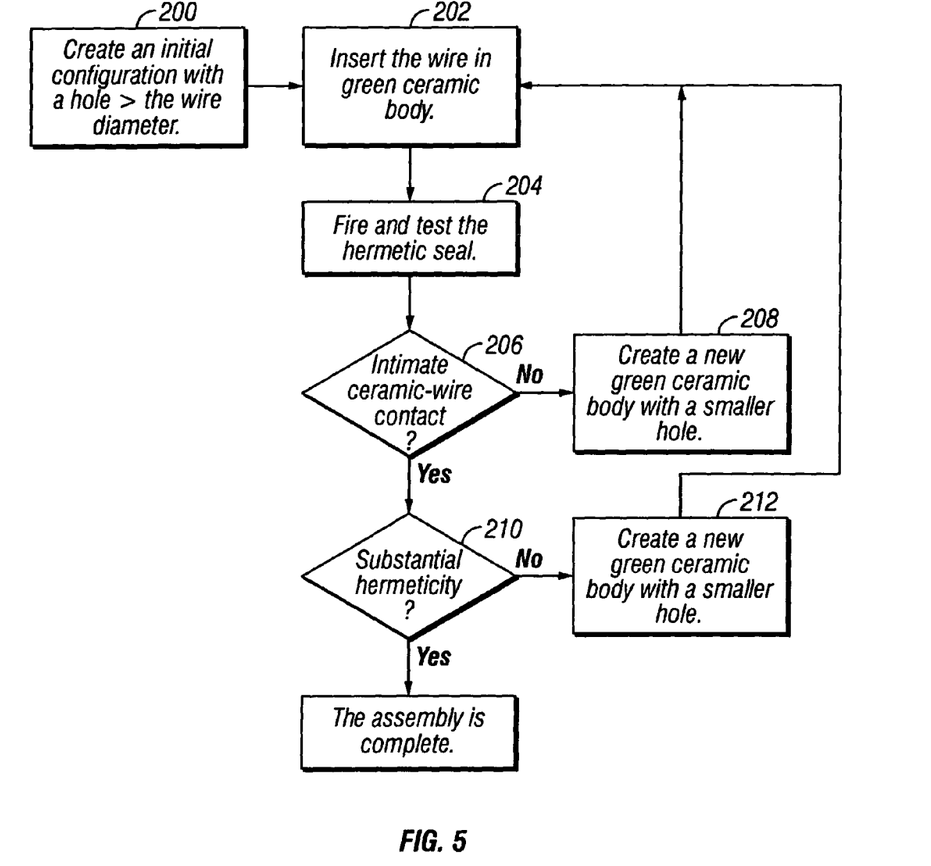
FIG. 5 is a flow diagram of an exemplary method of producing a substantially hermetic feedthrough in a ceramic body where an initial configuration includes the first diameter greater than the second diameter.

FIGS. 4 and 5 are flow diagrams that illustrate alternate embodiments of the method of the present invention. FIG. 4 illustrates an embodiment of a method for achieving a substantially hermetic feedthrough in a body where an initial configuration includes the first diameter less than, or equal to, the second diameter. FIG. 5 illustrates an embodiment of a method for achieving a substantially hermetic feedthrough in a body where an initial configuration includes the first diameter greater than the second diameter. These embodiments exemplify techniques that lead to substantially hermetic feedthroughs but are not inclusive of all possible methods for producing the invention described herein.

The following is a brief description of the embodiment illustrated in FIG. 4 of the method for creating a hermetic seal in a body having an initial configuration with the first diameter less than, or equal to, the second diameter. This embodiment is preferred if the green body appears ductile such that it may support sufficient plastic deformation to avoid cracking or other mechanical failure during wire insertion, however this case may also be implemented with brittle green bodies. The first step 100 is to create an initial configuration with a hole diameter less than, or equal to, the wire diameter. In step 102 the wire is inserted in the green ceramic body. The wire is inserted into the hole in the green body or directly into the green body without a pre-defined hole. In step 104 the existence of significant body damage is determined. If cracking or significant mechanical damage is visible, the first diameter is enlarged in step 106, iteratively, in new ceramic bodies until such mechanical damage is not observed upon wire insertion in step 102. Once a wire has been inserted into the green body without significant body damage the body is fired in step 108 and its hermetic seal is tested in step 110. If the seal is not substantially hermetic, the first diameter is again increased by creating a new green ceramic body with a larger hole in step 112 and steps 102, 104, 108, and 110 are repeated until substantial hermeticity is established in step 114 and the assembly is complete. Once the parameters for substantial hermeticity have been established, additional assemblies may be produced using the selected materials and determined dimensions.

The following is a brief description of the embodiment illustrated in FIG. 5 of the method for creating a hermetic seal in a body having an initial configuration with the first diameter greater than the second diameter. The embodiment of FIG. 5 is preferred if the green body appears brittle such that it may not support sufficient plastic deformation to avoid cracking or other gross mechanical failure during wire insertion, however this case may also be implemented with ductile green bodies. The first step 200 is to create an initial configuration with a hole diameter greater than the wire diameter. An initial configuration is chosen such that the first diameter is greater than the second diameter. In step 202 the wire is inserted into the hole in the green ceramic body. In step 204 the assembly is fired and inspected and then the hermetic seal is tested to ensure that the body is in intimate contact with the wire due to body shrinkage during sintering. In step 206 if intimate ceramic-wire contact is not observed, the first diameter is decreased in a new ceramic body in step 208, iteratively, in new ceramic bodies, and steps 202, 204, and 206 are repeated until intimate ceramic-wire contact is observed. The seal between the wire and the fired ceramic body is then tested in step 210. If the seal is not substantially hermetic, the first diameter is again decreased in a new ceramic body in step 212 and steps 202, 204, 206, and 210 are repeated until substantial hermeticity is established in step 214 and the assembly is complete. Once the parameters for substantial hermeticity have been established, additional assemblies may be produced using the selected materials and determined dimensions.

In accordance with another embodiment of the invention an implantable glucose-level sensing device 30 (FIG. 6) includes a generally circular or rectangular container 32 having a ceramic body 34 forming at least a portion thereof. The remainder 36 of the container 32 is preferably made of a metal such as titanium and is hermetically joined to the ceramic body 34 via brazing 38. Six electrodes 40, 42, 44, 46, 48 and 50 (FIG. 7) are formed on an exterior surface of the ceramic body 34 for contacting fluid in body tissue 52 (FIG. 6) when implanted. A plurality of feedthrough assemblies such as 54 are formed in the ceramic body 34, each electrically connected to a corresponding one of the electrodes. Each of the feedthrough assemblies 54 is constructed in the manner described in connection with FIGS. 1-3. Each of the feedthrough assemblies 54 directly contacts the ceramic body 34 to form a substantially hermetic seal between the ceramic body 34 and the feedthrough assemblies 54.

Referring again to FIG. 7, a reference electrode 40, a counter electrode 42, and a working electrode 44 form part of a glucose responsive detector portion of the sensing device 30. A working electrode 46, a counter electrode 48, and a reference electrode 50 form part of a background oxygen detector of the sensing device 30. A glucose oxidase element 55 is supported adjacent the working electrode 44.

Figure 6:
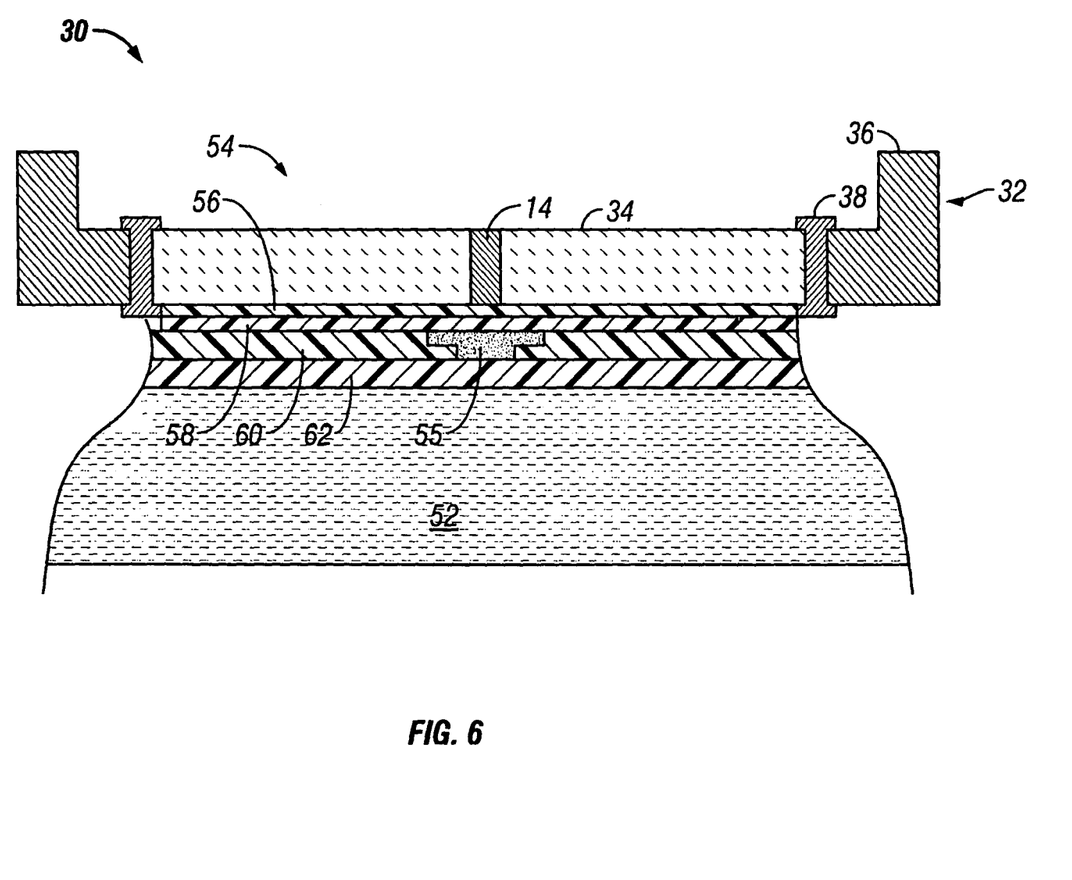
FIG. 6 is a diagrammatic vertical sectional view of an implantable glucose-level sensing device incorporating the feedthrough assembly of FIG. 3.
Figure 7:
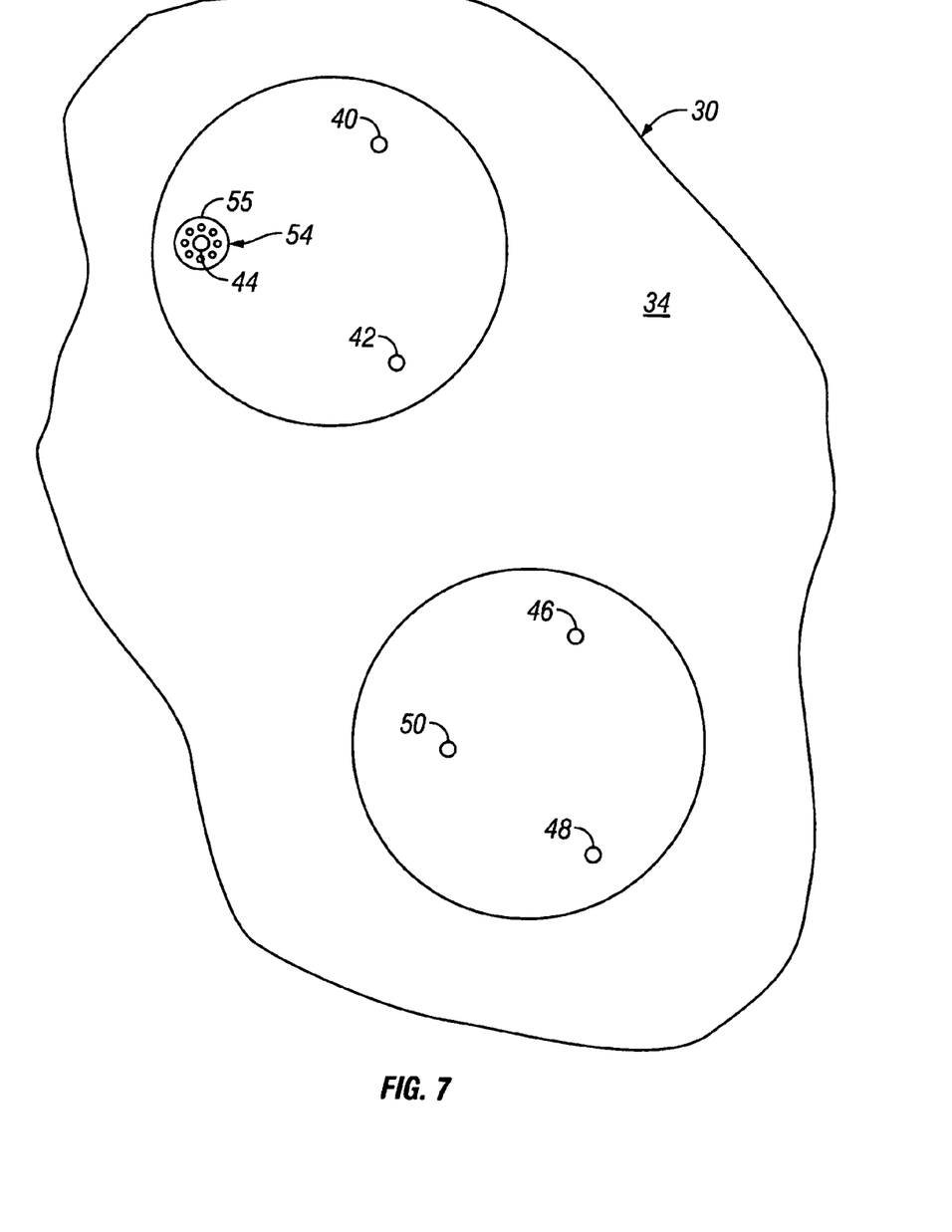
FIG. 7 is a fragmentary plan view of a portion of the exterior of the container of the sensing device of FIG. 6 illustrating the electrodes of its glucose-responsive detector and its optional background oxygen detector.

Referring to FIG. 6, an electrolyte gel layer 56, an internal polymer hydrophobic membrane 58, a silicone rubber layer 60 and an optional external membrane 62 are sandwiched together, overlie the exterior of the container 32, and surround the electrodes 40, 42, 44. Except for glucose oxidase element 55, these layers are not illustrated in FIG. 7. The electrolyte layer 56 (FIG. 6) maintains the electrodes 40, 42 and 44 in ionic contact with one another. Suitable techniques for preparation of the electrolyte gel layer 56 and the polymer hydrophobic membrane 58 are disclosed in U.S. Pat. No. 4,703,756 granted Nov. 3, 1987 to David A. Gough and Joseph Y. Lucisano et al., the entire disclosure of which is hereby incorporated by reference. See also U.S. Pat. No. 4,890,620 granted Jan. 2, 1990 to David A. Gough, the entire disclosure of which is hereby incorporated by reference.

The glucose oxidase element 55 may have a composite or laminate construction. Suitable constructions are disclosed in U.S. Patent Application No. US 2002/0156355 A1 of David A. Gough published Oct. 24, 2002, and U.S. Pat. No. 6,721, 587 granted to David A. Gough on Apr. 13, 2004, the entire disclosures of which are hereby incorporated by reference.

A circuit (not illustrated) is mounted inside the container 32 and is electrically connected to the electrodes via the feedthrough assemblies 54 and determines a glucose-level in a body fluid contacting the electrodes. Preferably the implanted sensing device 30 is battery powered and transmits information and receives instructions with respect to an electronic module outside the body via a radio frequency (RF) data link. See the circuitry illustrated in FIG. 6 of the aforementioned U.S. Pat. No. 4,703,756, for example. While the glucose responsive detector of sensing device 30 includes three electrodes, the reference electrode 40 and counter electrode 42 could be combined. The same is true of the background oxygen detector.

While we have described several embodiments of our invention, those skilled in the art will appreciate that it may be modified in both arrangement and detail. For example, whereas the wire 14 has a round cross-section, it could also have other cross-sectional shapes, including, but not limited to, uniform oval, square, and rectangular, as well as cross sections that vary in shape and size over the length of the wire. As another example, the wire could be of a branching structure, or it could follow a path through the ceramic body that was not straight. As another example, the green or fired ceramic body containing the wire could have additional layers of material, for example ceramic-based material, applied to one or both surfaces, either before, or after firing. As another example, the sensing device 30 is particularly suited for detecting glucose levels subcutaneously, but its basic structure can be modified to accommodate other electrochemical processes using different types of membranes and coatings, as well as other implantation locations. Also, the feedthrough structure 54 could be utilized to advantage in other instruments or devices requiring hermetic seals, including implantable medical devices such as pacemakers, neural stimulators, cochlear implants, and implantable hearing aids. Therefore, the protection afforded our invention should only be limited in accordance with the appended claims. Likewise, the following examples that illustrate particular embodiments are not intended to define the scope of the invention, which is limited only by the appended claims.

EXAMPLES

Green ceramic bodies of uniform thickness were prepared as follows:
1) Thickness (in inches in the green state): 0.013, 0.0195, 0.032, 0.050, 0.071 and 0.075.
2) Number of wires per body: 1 to 24
3) Hole diameter (inches): None, 0.002, 0.005, 0.0059, 0.006, 0.0063, 0.0079, 0.0087, 0.011, 0.016, 0.0135, 0.0160, 0.0197, 0.0217, 0.0236, 0.031
4) Ratio of (distance between holes) to (thickness of green body): range from 0.7 to 13.5

Each green ceramic body was formed from one of the following mixtures:
1. (1) 83% by volume ceramic powder (minimum 99.5% $Al_2O_3$, balance silica, talc, or wollastonite); and (2) 17% by volume organic polymer binder containing poly vinyl acetate and butyl benzyl phthalate plasticizer. This green mixture was used to form what is herein referred to as a ductile alumina green body. This mixture, after firing, meets or exceeds the material composition requirements of ASTM F 603-00.
2. (1) 81% by volume ceramic powder (minimum 99.5% $Al_2O_3$, ≤0.5% MgO, and ≤0.1% other oxides); and (2) 19% by volume wax-type organic polymer binder. This green mixture was used to form what is herein referred to as a brittle alumina green body. This mixture, after firing, meets or exceeds the material composition requirements of ASTM F 603-00.
3. (1) 79% by volume ceramic powder (a mixture of $ZrO_2$, $HfO_2$, and $Y_2O_3$, containing 4.5% to 5.4% $Y_2O_3$, ≤5% $HfO_2$, ≤0.5% $Al_2O_3$, and balance $ZrO_2$); and (2) 21% by volume organic polymer binder containing poly vinyl acetate and butyl benzyl phthalate plasticizer. This green mixture was used to form what is herein referred to as a zirconia green body. This mixture, after firing, meets the material composition requirements of ASTM F 1873.
4. (1) 79% by volume ceramic powder (a mixture of 18% to 22% $Al_2O_3$, 73% to 76% ($ZrO_2$ and $HfO_2$), and 4.14% to 4.16% $Y_2O_3$); and (2) 21% by volume organic binder containing poly vinyl acetate and butyl benzyl phthalate plasticizer. This green mixture was used to form what is herein referred to as an alumina-toughened zirconia or ATZ green body.

The bodies exhibited material properties in the green state which were categorized as either ductile or brittle. The ductile green bodies tend to deform without cracking during the wire insertion process, whereas the brittle green bodies were incapable of substantial plastic deformation. Features or holes in these bodies were produced by drilling with carbide twist drills, by laser-machining, or by sharp wire insertion without pre-defined holes.

Platinum wires, a minimum of 99.9% pure (Alfa Aesar), or alloyed wires containing 90% platinum and 10% iridium (Sigmund Cohn) of diameters 0.005, 0.006, 0.008, 0.014, 0.020, 0.030, 0.040 inches were cut to 0.5-inch lengths and sharpened to aid insertion. The sharpened wire parts were cleaned by sonication in a solution of 70% isopropanol in water and air-dried. For the wire insertion process, the green ceramic body was typically supported mechanically by a layer of silicone rubber at least 3/16 inch thick, with 1/8 inch holes aligned directly below the green ceramic body holes. The wires were introduced into the body in such a way that they completely penetrated the green body and the tapered region of the wire was exterior to the green body thickness.

Alternatively, platinum wires, a minimum of 99.9% pure (Alfa Aesar), or alloyed wires containing 90% platinum and 10% rhodium (Alfa Aesar) of diameters 0.002 and 0.005 inches were cut to lengths equal to the thickness of the green body into which they were inserted. The green body containing the wire was placed in a laminating mold and compressed to between 19,000 $lbs/in^2$ and 40,000 $lbs/in^2$ for between 2 and 30 minutes at between room temperature and 190° C.

The assemblies were fired to maximum temperatures between 1515° C. and 1700° C. These maximum temperatures were held for between 60 to 240 minutes before ramping down to room temperature. The firing profiles contained ramp rates between 1 and 10° C./min. Pre-sintering binder burnout was accomplished by executing profiles with dwells of up to 360 minutes at temperatures between 250° C. and 500° C. Success rates for achieving hermetic wire-to-body seals showed no dependence on ramp rate or dwell time for the abovementioned ranges.

Hermeticity was determined by measuring the helium leak rate of each wire-to-body seal using a Varian Multi-Test 947 helium leak detector. For the purpose of this set of examples, a hermetic seal between a wire and its ceramic body was defined as one which exhibited a helium leak rate of less than $1.0 \times 10^{-8}$ atm cc/s. Acceptable hermeticity of a group was defined as 90% or greater of the wire-to-body seals being hermetic by the abovementioned definition.

Results exemplifying combinations of materials, green body thicknesses, green body material properties, hole creation methods, hole sizes, wire materials, wire diameters, and test results are summarized below.

Example One

In this example, alumina green bodies 0.071-inch thick, exhibiting brittle material properties, were drilled with holes of 0.0079-inch diameter. Platinum wires of 0.008-inch diameter were placed in the 0.0079-inch diameter holes. In some cases, body cracking was observed upon wire insertion. The assemblies were fired and the seals were tested. Although some of the seals were hermetic, an acceptable success rate of hermeticity was not achieved.

A second set of alumina green bodies was created with the only difference being that holes were drilled 0.0087-inch in diameter. Platinum wires of 0.008-inch diameter were placed in the holes. The assemblies were fired and the seals were tested. Acceptable hermeticity was established.

The results of this example are provided in tabular form below:

| Example One | | | | | | | |
|---|---|---|---|---|---|---|---|
| Body material | Green body material properties | Green body thickness (inch) | Hole Type | Hole Diameter (inch) | Wire type | Wire Diameter (inch) | Hermeticity |
| Alumina | Brittle | 0.071 | Drilled | 0.0079 | Platinum | 0.008 | Not Acceptable |
| Alumina | Brittle | 0.071 | Drilled | 0.0087 | Platinum | 0.008 | Acceptable |

This example illustrates an iterative hole diameter optimization method of the invention.

Example Two

In this example, alumina green bodies 0.075-inch thick, exhibiting ductile material properties, were drilled with holes of 0.0063-inch and 0.0087-inch in diameter. Platinum wires of 0.006-inch and 0.008-inch diameter were placed in the 0.0063-inch and the 0.0087-inch holes, respectively. The assemblies were fired and the seals were tested. Acceptable hermeticity was established.

A second set of alumina green bodies was created with the only difference being holes that were drilled 0.0059-inch and 0.0079-inch in diameter. Platinum wires of 0.006-inch and 0.008-inch diameter were placed in the 0.0059-inch and the 0.0079-inch holes, respectively. The assemblies were fired and the seals were tested. Acceptable hermeticity was established. Although acceptable hermeticity was established in both cases, higher success rates were measured in the case in which the holes were drilled smaller than the wire diameter.

The results of this example are provided in tabular form below:

| Example Two | | | | | | | |
|---|---|---|---|---|---|---|---|
| Body material | Green body material properties | Green body thickness (inch) | Hole Type | Hole Diameter (inch) | Wire type | Wire Diameter (inch) | Hermeticity |
| Alumina | Ductile | 0.075 | Drilled | 0.0063 | Platinum | 0.006 | Acceptable |
| Alumina | Ductile | 0.075 | Drilled | 0.0059 | Platinum | 0.006 | Acceptable |
| Alumina | Ductile | 0.075 | Drilled | 0.0087 | Platinum | 0.008 | Acceptable |
| Alumina | Ductile | 0.075 | Drilled | 0.0079 | Platinum | 0.008 | Acceptable |

Example Three

Platinum wires of 0.005-inch diameter were pushed through ductile alumina green bodies with 0.032-inch and 0.050-inch thicknesses having no pre-defined holes. The assemblies were fired and the seals were tested. Acceptable hermeticity was established.

Platinum wires of 0.006-inch diameter were placed in holes drilled to 0.0063-inch diameter in brittle alumina green bodies 0.071-inch thick. The assemblies were fired and the seals were tested. Acceptable hermeticity was established.

Platinum wires of 0.008-inch diameter were placed in 0.032-inch thick ductile alumina green bodies drilled with 0.0079-inch holes and 0.050-inch thick ductile alumina green bodies drilled with 0.0079-inch holes. The assemblies were fired and the seals were tested. Acceptable hermeticity was established.

Platinum wires of 0.014-inch diameter were placed in 0.020-inch thick ductile alumina green bodies drilled with 0.011-inch holes, 0.032-inch thick ductile alumina green bodies drilled with 0.011-inch holes, 0.032-inch thick ductile alumina green bodies drilled with 0.0135-inch holes, and 0.075-inch thick ductile alumina green bodies drilled with 0.0135-inch holes. The assemblies were fired and the seals were tested. Acceptable hermeticity was established.

Platinum wires of 0.020-inch diameter were placed in 0.020-inch thick ductile alumina green bodies drilled with 0.016-inch holes, 0.032-inch thick ductile alumina green bodies with 0.0197-inch holes, and 0.075-inch thick ductile alumina green bodies with 0.0197-inch holes. The assemblies were fired and the seals were tested. Acceptable hermeticity was established.

The results of this example are provided in tabular form below:

Example Three

| Body material | Green body material properties | Green body thickness (inch) | Hole Type | Hole Diameter (inch) | Wire type | Wire Diameter (inch) | Hermeticity |
|---|---|---|---|---|---|---|---|
| Alumina | Ductile | 0.032 | Wire pushed | None | Platinum | 0.005 | Acceptable |
| Alumina | Ductile | 0.050 | Wire pushed | None | Platinum | 0.005 | Acceptable |
| Alumina | Brittle | 0.071 | Drilled | 0.0063 | Platinum | 0.006 | Acceptable |
| Alumina | Ductile | 0.032 | Drilled | 0.0079 | Platinum | 0.008 | Acceptable |
| Alumina | Ductile | 0.050 | Drilled | 0.0079 | Platinum | 0.008 | Acceptable |
| Alumina | Ductile | 0.020 | Drilled | 0.011 | Platinum | 0.014 | Acceptable |
| Alumina | Ductile | 0.032 | Drilled | 0.011 | Platinum | 0.014 | Acceptable |
| Alumina | Ductile | 0.032 | Drilled | 0.0135 | Platinum | 0.014 | Acceptable |
| Alumina | Ductile | 0.075 | Drilled | 0.0135 | Platinum | 0.014 | Acceptable |
| Alumina | Ductile | 0.020 | Drilled | 0.016 | Platinum | 0.020 | Acceptable |
| Alumina | Ductile | 0.032 | Drilled | 0.0197 | Platinum | 0.020 | Acceptable |
| Alumina | Ductile | 0.075 | Drilled | 0.0197 | Platinum | 0.020 | Acceptable |

Example Four

Wires of alloyed platinum and iridium, 0.006-inch in diameter, were placed in holes drilled to 0.0059-inch diameter in ductile alumina green bodies 0.020-inch thick. The assemblies were fired and the seals were tested. Acceptable hermeticity was established.

The results of this example are provided in tabular form below:

Example Four

| Body material | Green body material properties | Green body thickness (inch) | Hole Type | Hole Diameter (inch) | Wire type | Wire Diameter (inch) | Hermeticity |
|---|---|---|---|---|---|---|---|
| Alumina | Ductile | 0.020 | Drilled | 0.0059 | Platinum-iridium alloy | 0.006 | Acceptable |

Example Five

Platinum wires of 0.005-inch diameter were placed in 0.020-inch thick ductile zirconia green bodies laser-bored with 0.003-inch holes. The assemblies were fired and the seals were tested. Acceptable hermeticity was established.

Platinum wires of 0.008-inch diameter were placed in 0.013-inch thick ductile zirconia green bodies laser-bored with 0.005 holes. The assemblies were fired and the seals were tested. Acceptable hermeticity was established.

Platinum wires of 0.014-inch diameter were placed in 0.013-inch thick ductile zirconia green bodies drilled with 0.011-inch holes. The assemblies were fired and the seals were tested. Acceptable hermeticity was established.

Platinum wires of 0.030-inch diameter were placed in 0.075-inch thick ductile zirconia green bodies drilled with 0.0236-inch holes. The assemblies were fired and the seals were tested. Acceptable hermeticity was established.

Platinum wires of 0.040-inch diameter were placed in 0.075-inch thick ductile zirconia green bodies drilled with 0.031-inch holes. The assemblies were fired and the seals were tested. Acceptable hermeticity was established.

The results of this example are provided in tabular form below:

| Body material | Green body material properties | Green body thickness (inch) | Hole Type | Hole Diameter (inch) | Wire type | Wire Diameter (inch) | Hermeticity |
|---|---|---|---|---|---|---|---|
| Zirconia | Ductile | 0.020 | Laser-bored | 0.003 | Platinum | 0.005 | Acceptable |
| Zirconia | Ductile | 0.013 | Laser-bored | 0.005 | Platinum | 0.008 | Acceptable |
| Zirconia | Ductile | 0.013 | Drilled | 0.011 | Platinum | 0.014 | Acceptable |
| Zirconia | Ductile | 0.075 | Drilled | 0.0236 | Platinum | 0.030 | Acceptable |
| Zirconia | Ductile | 0.075 | Drilled | 0.031 | Platinum | 0.040 | Acceptable |

Example Six

Twenty-four wires of alloyed platinum and iridium of 0.005-inch diameter were placed into twenty-four different laser-machined holes 0.002-inch in diameter in a 0.015-inch thick ductile alumina green body. The assembly was fired and the seals were tested. Acceptable hermeticity was established.

The results of this example are provided in tabular form below:

| Body material | Green body material properties | Green body thickness (inch) | Hole Type | Hole Diameter (inch) | Wire type | Wire Diameter (inch) | Hermeticity |
|---|---|---|---|---|---|---|---|
| Alumina | Ductile | 0.015 | 24 locations, laser-bored | 0.002 | Platinum-iridium alloy | 0.005 | Acceptable |

Example Seven

Platinum wires of 0.005-inch diameter were placed in 0.026-inch thick ductile ATZ green bodies laser-machined with 0.004-inch holes. These assemblies were fired and the seals were tested. Acceptable hermeticity was established.

The results of this example are provided in tabular form below:

| Body material | Green body material properties | Green body thickness (inch) | Hole Type | Hole Diameter (inch) | Wire type | Wire Diameter (inch) | Hermeticity |
|---|---|---|---|---|---|---|---|
| ATZ | Ductile | 0.026 | Laser-bored | 0.004 | Platinum | 0.005 | Acceptable |

Example Eight

Platinum wires of 0.005-inch diameter were placed in 0.071-inch thick ductile alumina green bodies laser-machined with 0.006-inch holes. The assemblies were pressed in a laminating mold at 190° C. for 30 minutes at 11,000 lbs/in$^2$ pressure. These conditions were sufficient to establish intimate contact between the wire and the green body. The assemblies were fired and the seals were tested. Acceptable hermeticity was established.

The results of this example are provided in tabular form below:

| | | | | | | | |
|---|---|---|---|---|---|---|---|
| | Example Eight | | | | | | |
| Body material | Green body material properties | Green body thickness (inch) | Hole Type | Hole Diameter (inch) | Wire type | Wire Diameter (inch) | Hermeticity |
| Alumina | Ductile | 0.071 | Laser-bored, then pressed | 0.006 before pressing | Platinum | 0.005 | Acceptable |

Example Nine

Platinum wires of 0.002-inch diameter were placed in 0.006-inch diameter holes that were drilled in 0.075-inch thick brittle alumina green bodies. These assemblies were pressed in a closed laminating mold at room temperature for 2 minutes at 40,000 lbs/in$^2$ pressure. These conditions were sufficient to establish intimate contact between the wire and the green body. The assemblies were fired and the seals were tested. Acceptable hermeticity was established.

The results of this experiment are provided in tabular form below:

| | | | | | | | |
|---|---|---|---|---|---|---|---|
| | Example Nine | | | | | | |
| Body material | Green body material properties | Green body thickness (inch) | Hole Type | Hole Diameter (inch) | Wire type | Wire Diameter (inch) | Hermeticity |
| Alumina | Brittle | 0.075 | Drilled, then pressed | 0.006 before pressing | Platinum | 0.002 | Acceptable |

Example Ten

Wires of alloyed platinum and rhodium of 0.005-inch diameter were placed in 0.006-inch diameter holes that were drilled in 0.075-inch thick brittle alumina green bodies. These assemblies were pressed in a closed laminating mold at room temperature for 2 minutes at 19,000 lbs/in$^2$ pressure. These conditions were sufficient to establish intimate contact between the wire and the green body. The assemblies were fired and the seals were tested. Acceptable hermeticity was established.

The results of this experiment are provided in tabular form below:

| Body material | Green body material properties | Green body thickness (inch) | Hole Type | Hole Diameter (inch) | Wire type | Wire Diameter (inch) | Hermeticity |
|---|---|---|---|---|---|---|---|
| Alumina | Brittle | 0.075 | Drilled, then pressed | 0.006 before pressing | Platinum-rhodium alloy | 0.005 | Acceptable |

Example Eleven

Multi-conductor feedthrough assemblies, fabricated in accordance with the methods of the invention, consisting of ceramic bodies with a plurality of substantially hermetic feedthroughs were subjected to a thermal-shock test. The thermal-shock test consisted of cycling the temperature of the multi-conductor feedthrough assemblies between 0° C. and 100° C. by transferring the multi-conductor feedthrough assemblies from a boiling-water bath to an ice-water bath and then back to the boiling-water bath a total of fifteen times. In substantial accordance with the methods of MIL-STD-883G Method 1011.9 "Thermal Shock", the multi-conductor feedthrough assemblies were held in each bath for a dwell time greater than two minutes with less than ten seconds of transfer time between the baths. The multi-conductor feedthrough assemblies were dried, by baking, for greater than one hour at 150° C., cooled to room temperature, and then subjected to a helium-leak test.

Multi-conductor feedthrough assemblies were produced from 0.071-inch thick brittle alumina green bodies and platinum wires of 0.008-inch diameter. These multi-conductor feedthrough assemblies were subjected to the thermal-shock test. Acceptable hermeticity was maintained.

Multi-conductor feedthrough assemblies were produced from 0.075-inch thick ductile green alumina bodies and platinum wires of 0.006-inch diameter. These multi-conductor feedthrough assemblies were subjected to the thermal-shock test. Acceptable hermeticity was maintained.

Multi-conductor feedthrough assemblies were produced from 0.075-inch thick ductile green alumina bodies and platinum wires of 0.014-inch diameter. These multi-conductor feedthrough assemblies were subjected to the thermal-shock test. Acceptable hermeticity was maintained.

The results of this experiment are provided in tabular form below:

Example Eleven

| Body material | Green body material properties | Green body thickness (inch) | Feedthrough Type | Wire type | Wire diameter (inch) | Post-thermal-shock hermeticity |
|---|---|---|---|---|---|---|
| Alumina | Brittle | 0.071 | Multi-conductor | Platinum | 0.008 | Acceptable |
| Alumina | Ductile | 0.075 | Multi-conductor | Platinum | 0.006 | Acceptable |
| Alumina | Ductile | 0.075 | Multi-conductor | Platinum | 0.014 | Acceptable |

We claim:

1. A method of forming a feedthrough assembly, comprising the steps of:
    providing a green ceramic body;
    forming a through hole in the green ceramic body having a first diameter;
    inserting a corrosion-resistance solid wire through the hole, the wire comprising a material selected from the group consisting of platinum, palladium, rhodium, iridium, osmium and alloys of platinum, palladium, rhodium, iridium, and osmium and the wire having a second diameter;
    firing the green ceramic body to sinter the green ceramic body; and
    the first and second diameters being selected such that cracking of the sintered ceramic body adjacent the wire as a result of dimensional changes of the green ceramic body during firing is avoided and a substantially hermetic seal is formed between the sintered ceramic body and the wire, wherein the green ceramic body has a thickness of at least 0.050 inches thick.

2. The method of claim 1 and further comprising the step of forming an electrode on a first end of the wire.

3. The method of claim 2 wherein the electrode is substantially coplanar with a surface of the sintered ceramic body.

4. The method of claim 1 wherein the hermetic seal is a diffusion bond between the metal wire and the sintered ceramic body.

5. The method of claim 1 wherein the wire has a diameter of less than about 0.020 inches.

6. The method of claim 1 wherein the sintered ceramic body comprises compounds selected from the group consisting of oxides, carbides, borides, nitrides and silicides of aluminum, zirconium, beryllium, silicon, titanium, yttrium, hafnium, magnesium, and zinc.

7. The method of claim 1 wherein the sintered ceramic body has a thickness of less than about 0.10 inches.

8. The method of claim 1 wherein the wire has a diameter of less than about 0.020 inches and the sintered ceramic body has a thickness of less than about 0.10 inches.

9. The method of claim 1 and further comprising the step of forming a contact pad on a second end of the wire.

10. A method of forming a feedthrough assembly in a ceramic body, comprising the steps of:
    providing a green ceramic body that surrounds corrosion-resistance solid wire extending through the green ceramic body, the wire comprising a material selected from the group consisting of platinum, palladium, rhodium, iridium, osmium and alloys of platinum, palladium, rhodium, iridium, and osmium; and
    firing the green ceramic body to sinter the green ceramic body;
    whereby cracking of the sintered ceramic body adjacent the wire as a result of dimensional changes of the green ceramic body during firing is avoided and a substantially hermetic seal is formed between the sintered ceramic body and the wire, wherein the green ceramic body has a thickness of at least 0.050 inches thick.

11. The method of claim 10 wherein a hole with a first diameter is formed in the green ceramic body before the wire having a second diameter is inserted through the hole, and further wherein the first diameter is less than or equal to the second diameter.

12. The method of claim 10 wherein a hole with a first diameter is formed in the green ceramic body before the wire having a second diameter is inserted through the hole, and further wherein the first diameter is greater than the second diameter.

13. The method of claim 10 wherein the ceramic body comprises compounds selected from the group consisting of oxides, carbides, borides, nitrides and silicides of aluminum, zirconium, beryllium, silicon, titanium, yttrium, hafnium, magnesium, and zinc.

14. The method of claim 10 wherein the green ceramic body has no pre-formed hole and the wire is inserted through the green ceramic body.

15. The method of claim 10 wherein the green ceramic body is formed around the wire by pressing the green ceramic body in a mold.

* * * * *